(12) United States Patent
Mikhailov

(10) Patent No.: US 9,878,890 B2
(45) Date of Patent: Jan. 30, 2018

(54) UNIVERSAL CONTAINER CAPPER/DECAPPER

(75) Inventor: Sergey Mikhailov, Cockeysville, MD (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 865 days.

(21) Appl. No.: 13/129,199

(22) PCT Filed: Nov. 16, 2009
(Under 37 CFR 1.47)

(86) PCT No.: PCT/CA2009/001643
§ 371 (c)(1),
(2), (4) Date: Mar. 29, 2012

(87) PCT Pub. No.: WO2010/054480
PCT Pub. Date: May 20, 2010

(65) Prior Publication Data
US 2012/0304597 A1    Dec. 6, 2012

Related U.S. Application Data

(60) Provisional application No. 61/115,002, filed on Nov. 14, 2008.

(51) Int. Cl.
*B67B 7/18* (2006.01)
*B67B 3/20* (2006.01)
(Continued)

(52) U.S. Cl.
CPC .............. *B67B 7/182* (2013.01); *B67B 3/20* (2013.01); *B01L 3/50825* (2013.01); *G01N 2035/0405* (2013.01)

(58) Field of Classification Search
USPC .................................................. 294/118, 119
See application file for complete search history.

(56) References Cited

U.S. PATENT DOCUMENTS 1,510,913 A * 10/1924 Arey .................. B67B 3/20
53/287
3,771,284 A * 11/1973 Boeckmann .......... B67B 3/2033
53/282
(Continued)

FOREIGN PATENT DOCUMENTS

FR      2658587 A1      8/1991
GB       601622 A  *   5/1948 ............. B67B 7/182
WO    2009016502 A1    2/2009

OTHER PUBLICATIONS

International Search Report and Written Opinion, PCT/CA2009/001643, dated Feb. 25, 2010.
(Continued)

*Primary Examiner* — Stephen F Gerrity
*Assistant Examiner* — Mary Hibbert
(74) *Attorney, Agent, or Firm* — Botos Churchill IP Law LLP

(57) ABSTRACT

A universal container capper/decapper includes a capper/decapper assembly, and an axial actuator. The capper/decapper assembly comprises a capper/decapper housing, and at least one gripper arm. The capper/decapper housing has an axis of rotation. Each gripper arm has a driven end, a gripper end, and a knee portion intermediate the driven end and the gripper end. Each gripper arm is pivotally coupled to the housing proximate the knee portion. The axial actuator is coupled to each driven end and is configured to drive each gripper end in a radial direction relative to the axis of rotation by rotating each gripper arm about the respective knee portion relative to the housing.

22 Claims, 14 Drawing Sheets

(51) Int. Cl.
　　　*G01N 35/04*　　　(2006.01)
　　　*B01L 3/00*　　　(2006.01)

(56) References Cited

U.S. PATENT DOCUMENTS

| | | | |
|---|---|---|---|
| 3,852,941 A * | 12/1974 | Bross | B65B 7/2835 |
| | | | 53/317 |
| 4,085,632 A | 4/1978 | Hogan et al. | |
| 4,265,071 A | 5/1981 | Smith et al. | |
| 4,299,072 A * | 11/1981 | Holstein | B67B 3/2033 |
| | | | 475/11 |
| 5,479,762 A * | 1/1996 | Bliss | B67B 3/06 |
| | | | 53/317 |
| 5,647,251 A | 7/1997 | Hardman | |
| 5,709,120 A * | 1/1998 | Shilling | 72/290 |
| 6,477,919 B1 | 11/2002 | Thomas et al. | |
| 7,024,965 B2 | 4/2006 | Tremblay | |
| 7,040,194 B2 | 5/2006 | Wu et al. | |
| 7,972,579 B2 * | 7/2011 | Brunner | 422/560 |
| 2006/0272284 A1 * | 12/2006 | Galimberti | B67B 3/28 |
| | | | 53/75 |

OTHER PUBLICATIONS

Supplementary European Search Report for Application No. EP09825689 dated Aug. 28, 2015.

* cited by examiner

UNIVERSAL CONTAINER CAPPER/DECAPPER

CROSS REFERENCE TO RELATED APPLICATIONS

The present application is a national phase entry under 35 U.S.C. § 371 of International Application No. PCT/CA2009/001643, filed Nov. 16, 2009, published in English, which claims the benefit of the filing date of U.S. Provisional Patent Application Ser. No. 61/115,002, entitled "Universal Container Capper/Decapper", filed Nov. 14, 2008, the disclosures of said applications are incorporated by reference herein.

FIELD

This patent application relates to an apparatus for decapping and recapping containers. In particular, this patent application relates to a container decapper/capper that can remove and replace and the screw-on cap of a container.

BACKGROUND

Specimen containers are used in laboratory environments for storing and transporting specimens to be tested. Specimen containers come in a variety of sizes depending on the characteristics or the amount of a specimen needing to be stored or transported. Industry standards may also dictate the type of container to be used for transporting a particular specimen.

Multiple sizes of specimen containers may be delivered to a laboratory for specimen testing. The containers are typically sealed with a screw-on container cap. Therefore, testing specimens is typically a time-consuming and labour-intensive process, requiring removal of the cap, extraction of a specimen sample from the container, and re-installation of the cap.

Hogan (U.S. Pat. No. 4,085,632) describes a screw cap opener for jars having screw caps or lids thereon. The cap opener consists of a plastic holder that has a pair of nickel-plated metal blades that are mounted to the holder to form a V-shaped gripping structure. The V-shaped configuration allows jar lids of various sizes to be accommodated.

Hardman (U.S. Pat. No. 5,647,251) describes an automatic jar opener comprising a top retainer that holds the jar cap, and a bottom jar retainer that holds the jar. The bottom jar retainer includes substantially horizontal clamps that are movable in a horizontal plane between an open position and a clamping position. A vertical drive adjusts the vertical position of the bottom jar retainer relative to the top jar retainer. A twisting force is applied to the jar cap by the top jar retainer while the bottom jar retainer holds the jar.

Tremblay (U.S. Pat. No. 7,024,965) describes a semi-automatic jar opener comprising an upper turntable and a lower turntable. The upper and lower turntables are each provided with a pair of opposing jaws that are coupled to a central gear via respective rack elements. A jar is inserted between the upper and lower turntables, and the upper turntable is brought against the jar cover. A motor coupled to the lower turntable causes the lower turntable to rotate, thereby causing the jar and upper turntable to rotate. Rotation of the turntables causes the jaws of the upper turntable to move radially inwards towards the jar cover, and the jaws of the lower turntable to move radially inwards towards the jar. Further rotation of the jar cover is prevented when the jaws of the upper turntable engage the jar cover, thereby causing the lower turntable to unscrew the jar from the jar cover.

Wu (U.S. Pat. No. 7,040,194) describes a jar/bottle opener having a housing, a first pair of opposed jaws for gripping a jar or bottle and a second pair of opposed jaws for gripping a jar or bottle closure. A driven shaft operates the first and second jaws and turns the second jaws relative to the first jaws.

SUMMARY

As described in this patent application, the universal container capper/decapper includes a capper/decapper assembly, and an axial actuator. The capper/decapper assembly comprises a capper/decapper housing, and at least one gripper arm. The capper/decapper housing has an axis of rotation. Each gripper arm has a driven end, a gripper end, and a knee portion intermediate the driven end and the gripper end. Each gripper arm is pivotally coupled to the housing proximate the knee portion. The axial actuator is coupled to each driven end and is configured to drive each gripper end in a radial direction relative to the axis of rotation by rotating each gripper arm about the respective knee portion relative to the housing.

In one implementation, the axial actuator is configured to rotate each gripper arm by driving each driven end in a direction substantially parallel to the axis of rotation. The capper/decapper assembly may also comprise a yoke that is disposed within the housing. The driven ends may be pivotally coupled to the yoke, and the axial actuator may comprise a rod actuator that is coupled to the yoke and is configured to drive each driven end by moving the yoke in a direction substantially parallel to the axis of rotation.

The rod actuator may comprise an elongate shaft that is coupled to the yoke, and a linear actuator that is coupled to the elongate shaft. The rod actuator may also comprise a spring actuator mechanism that is coupled to the elongate shaft and is configured to urge each gripper end radially inwards. The spring actuator mechanism may comprise a coil spring that is disposed around the elongate shaft and is coupled at one end to the elongate shaft and at an opposite end to the capper/decapper housing.

In one implementation, the capper/decapper housing comprises a side wall that has at least one radially-extending channel. Each gripper arm is pivotally received within a respective one of the radially-extending channels.

The capper/decapper housing may also comprise a base plate that is disposed at a bottom end of the side wall. The base plate may comprise at least one radially-extending slot. Each radially-extending slot is aligned with a respective one of the radially-extending channels and is configured to receive a respective gripper end therein.

The container capper/decapper may also include a rotational actuator that is coupled to the axial actuator for rotating the capper/decapper assembly about the axis of rotation.

The container capper/decapper may include a plurality of the gripper arms, disposed substantially equidistantly around the capper/decapper housing. The gripper arms may have a substantially L-shape.

BRIEF DESCRIPTION OF THE DRAWINGS

The aforementioned features will now be described, by way of example, with reference to the accompanying drawings, in which.

DETAILED DESCRIPTION

The drawings depict a universal capper/decapper, denoted generally as 100, that comprises a capper/decapper assembly 102, and an axial actuator 104. The capper/decapper assembly 102 comprises a capper/decapper housing 106, and at least one gripper arm 108.

Figure 9:
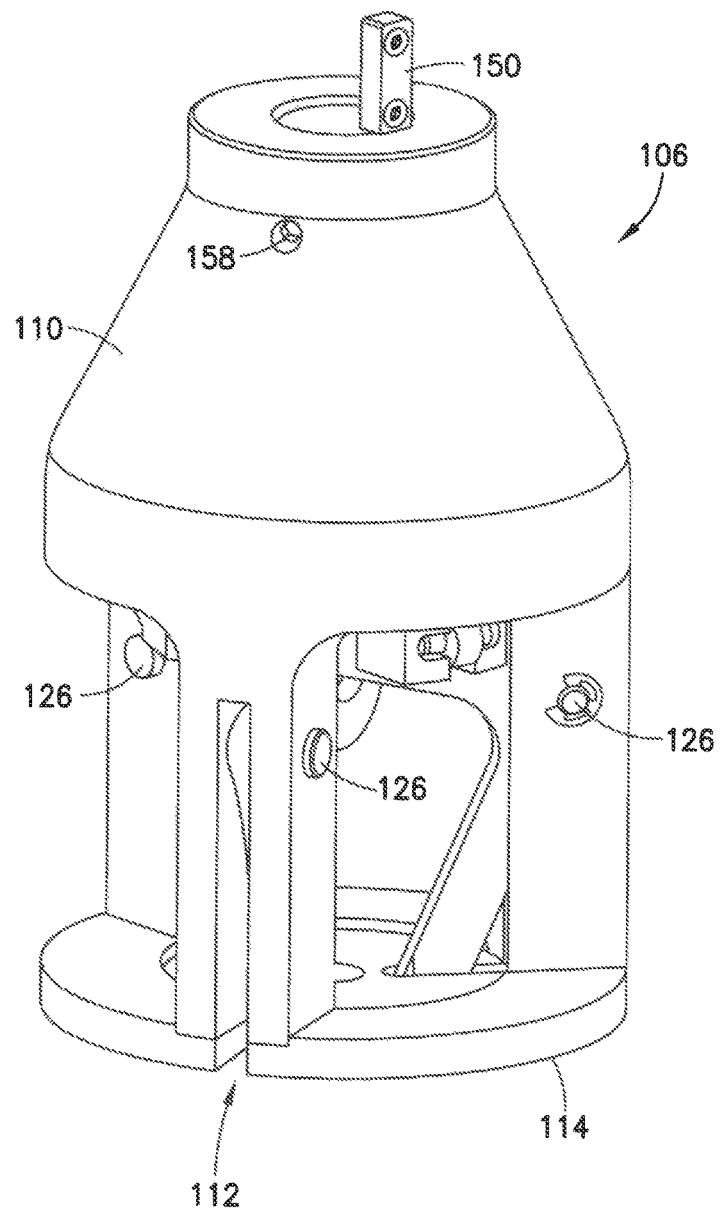
FIG. 9 is a magnified side perspective view of the capper/decapper housing.
Figure 10:
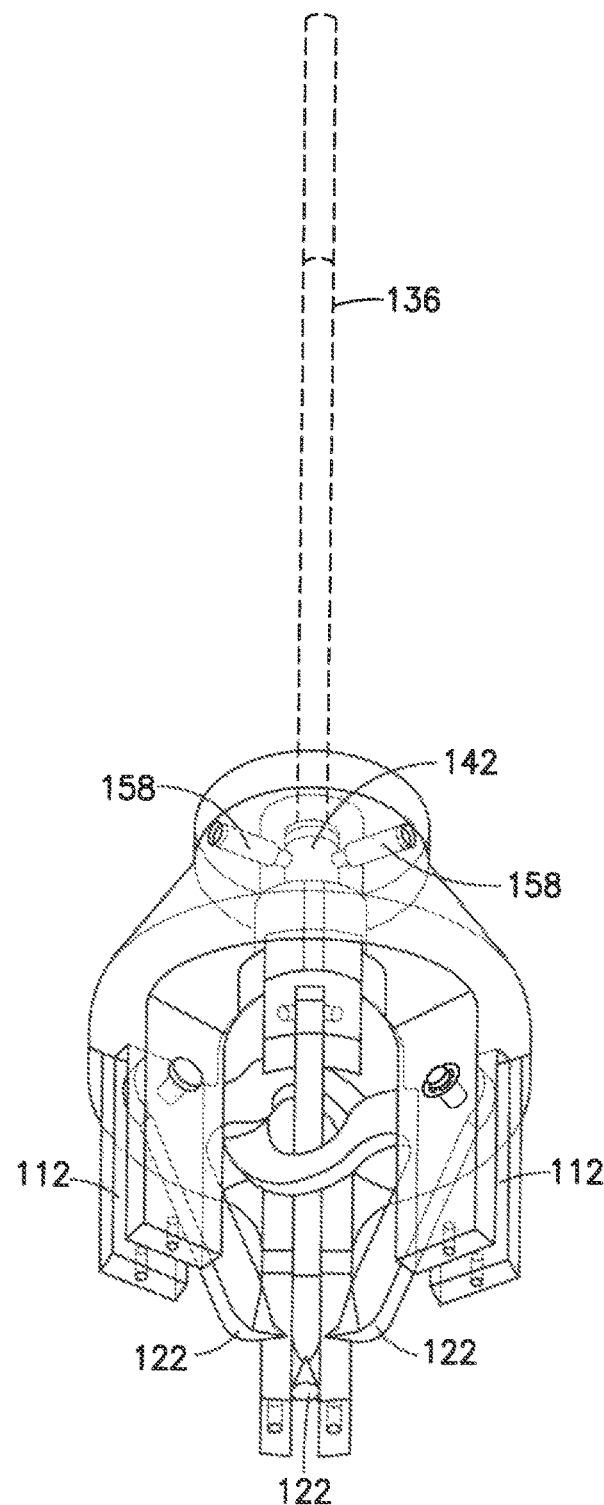
FIG. 10 is a bottom perspective view of the universal capper/decapper shown in FIG. 8, with the base plate removed and the capper/decapper being transparently depicted.

The capper/decapper housing 106 has an axis of rotation, a pair of opposite ends, and a side wall 110 that extends between the opposite ends. Preferably, the side wall 110 is substantially continuous proximate the upper end of the housing 106, and includes at least one radially-extending channel 112 proximate the lower end of the capper/decapper housing 106. The gripper arm 108 is pivotally received within the radially-extending channel 112. As shown in FIG. 9, preferably the channel 112 is oriented substantially parallel to the axis of rotation of the capper/decapper housing 106.

Figure 1:
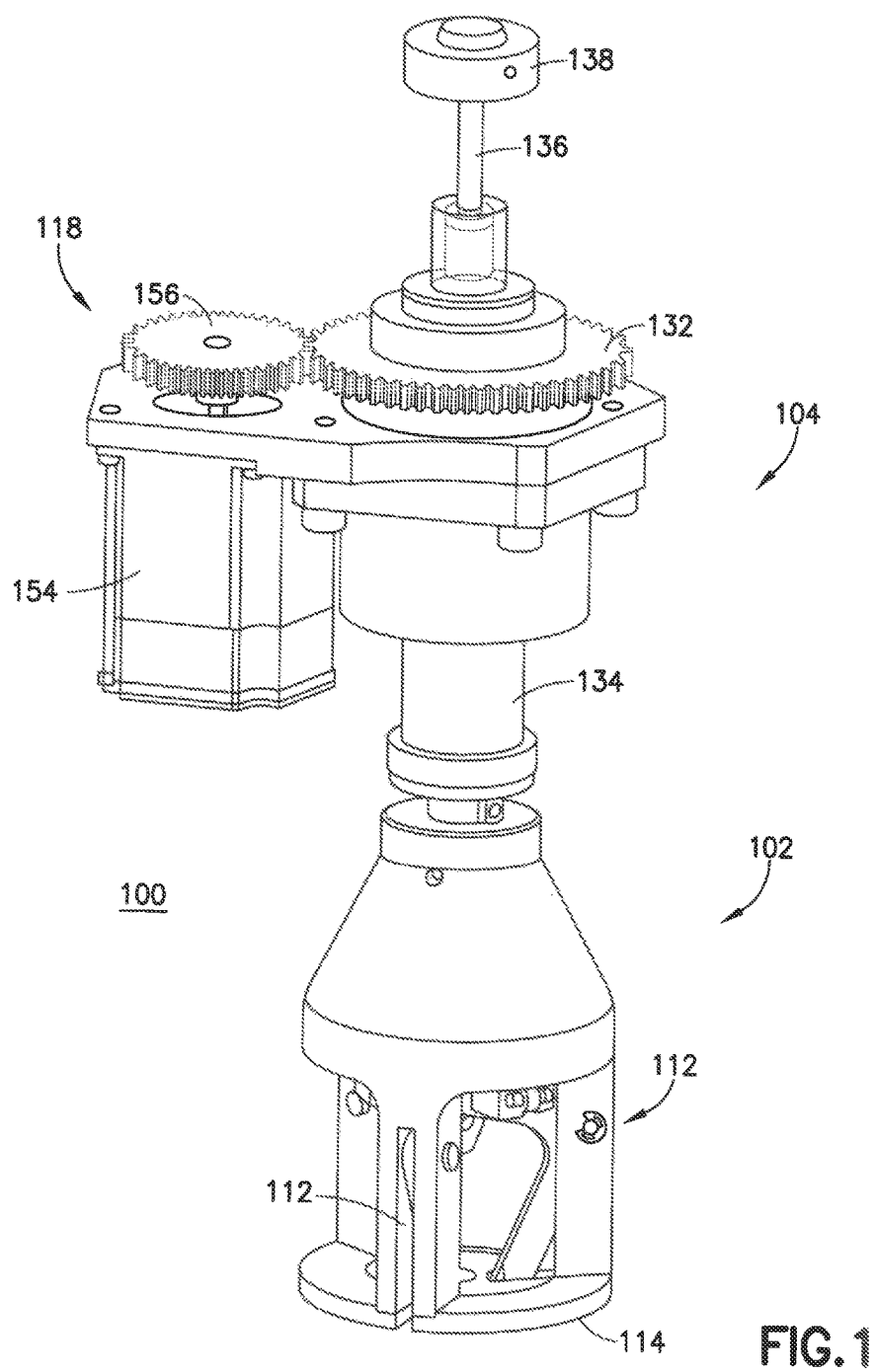
FIG. 1 is a side perspective view of the universal capper/decapper, showing the gripper arms and the primary and rotational actuators.
Figure 2:
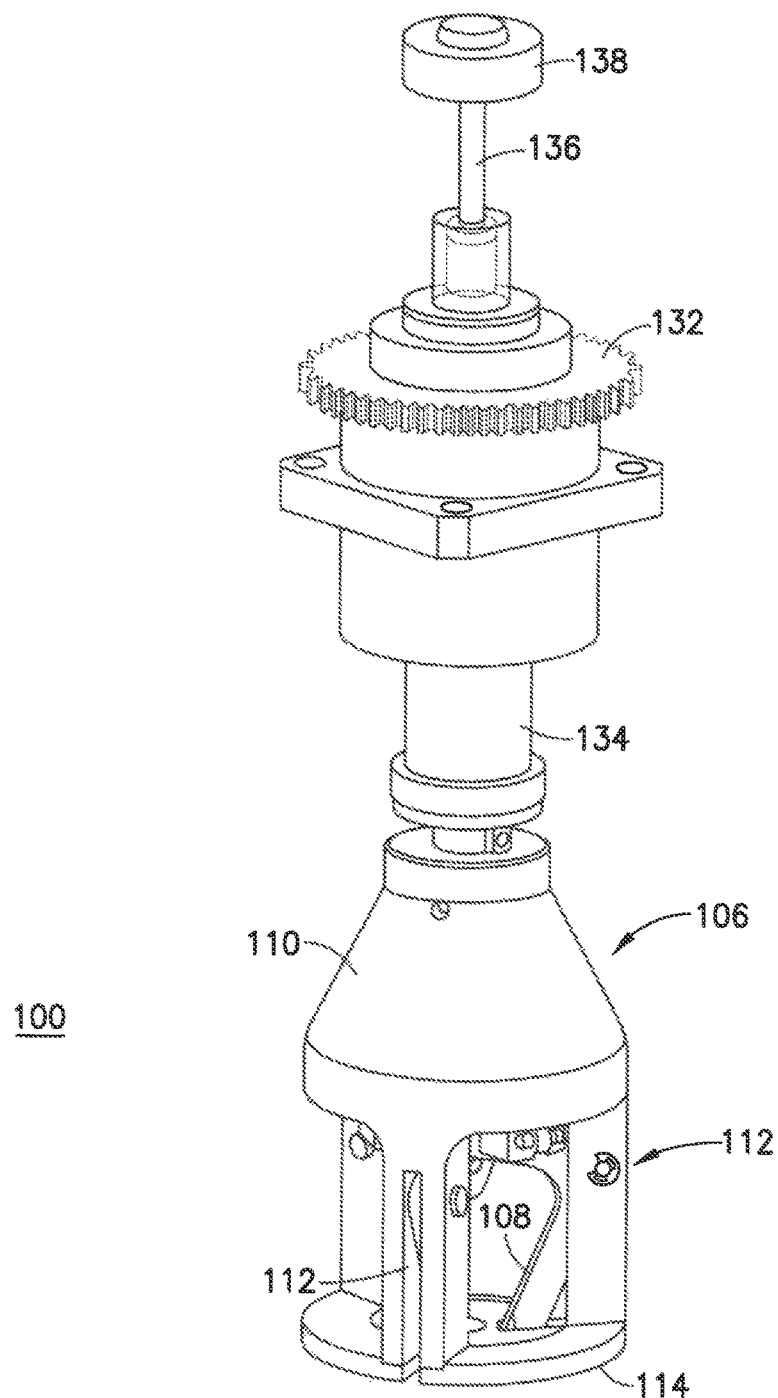
FIG. 2 is a perspective view of the universal capper/decapper shown in FIG. 1, with the rotational actuator removed.
Figure 3:
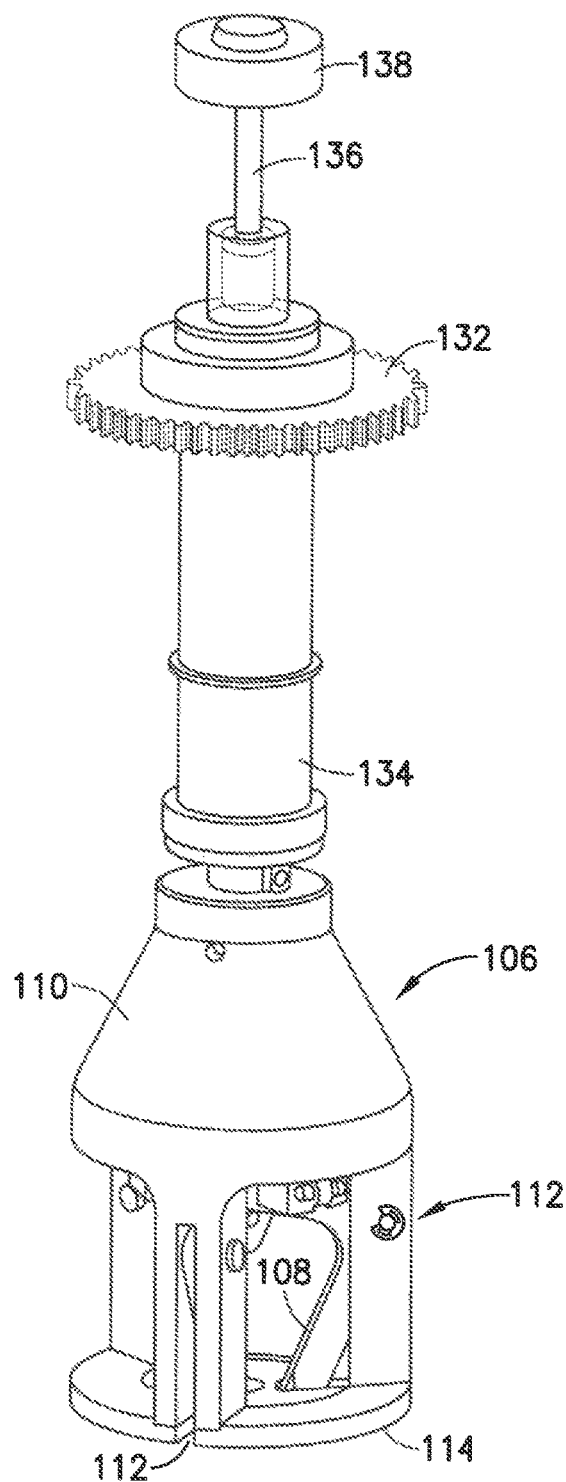
FIG. 3 is a perspective view of the universal capper/decapper shown in FIG. 2, with the rotational actuator mount removed.
Figure 4:
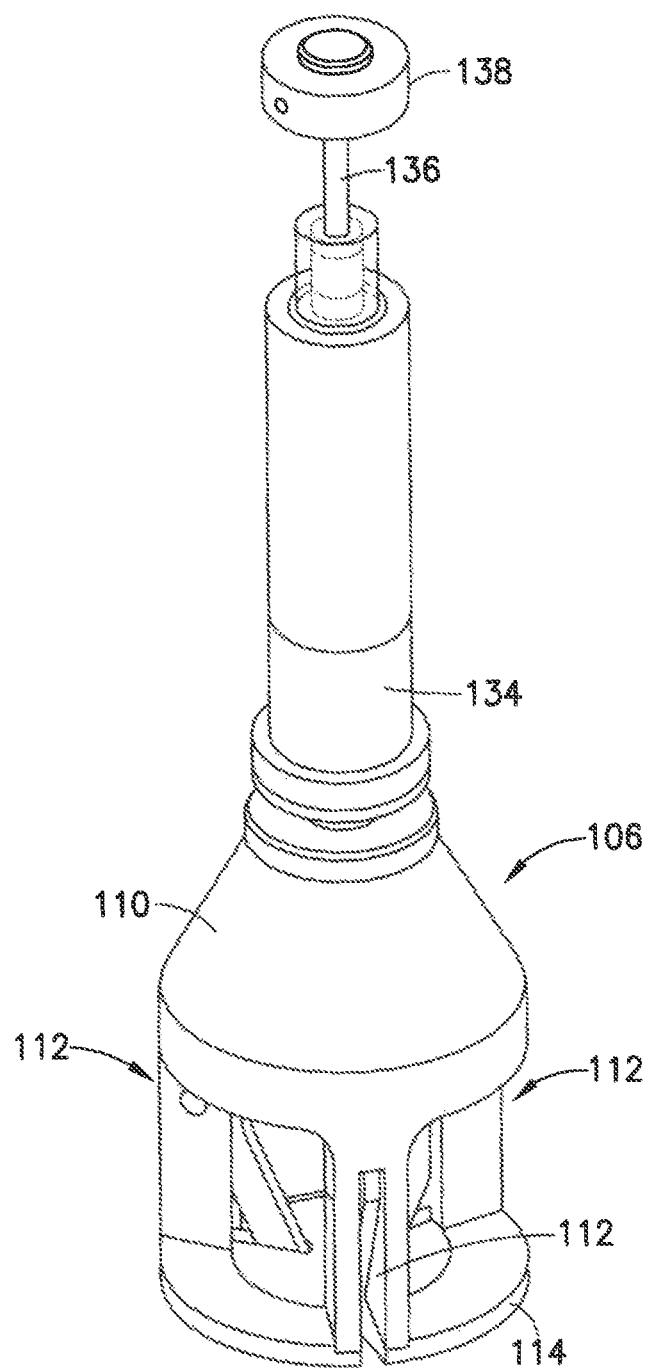
FIG. 4 is a perspective view of the universal capper/decapper shown in FIG. 3, with the driven gear of the rotational actuator removed.
Figure 5:
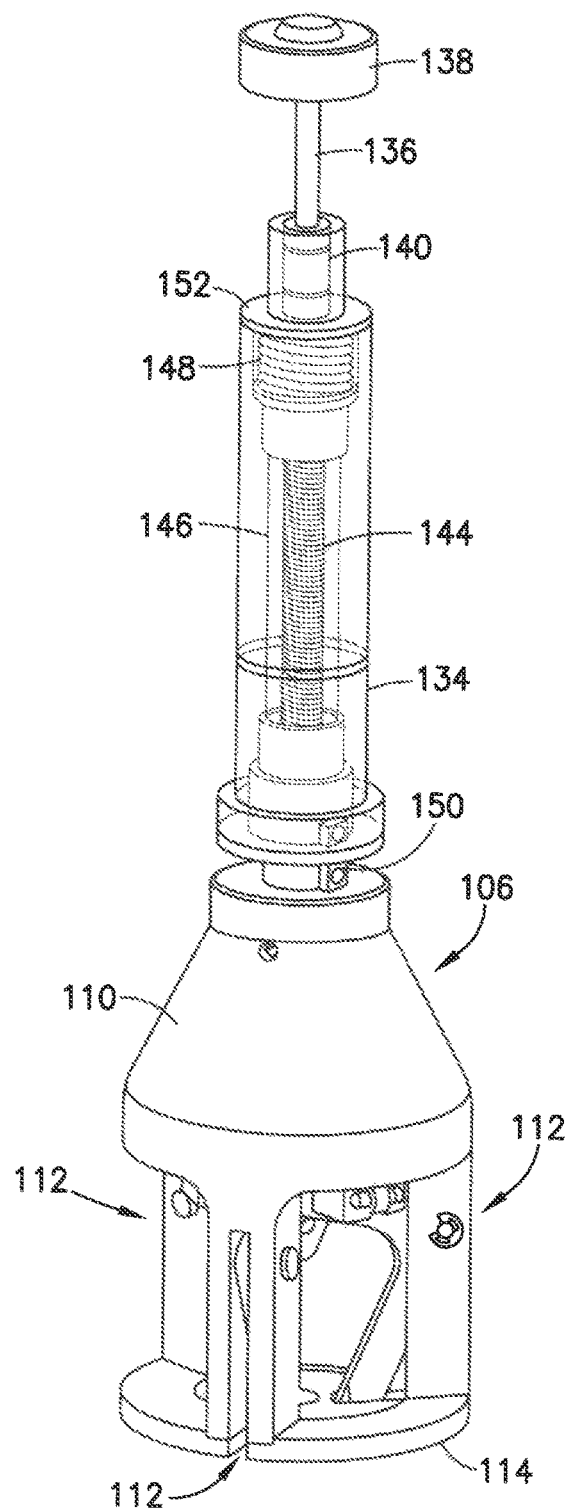
FIG. 5 is a perspective view of the universal capper/decapper shown in FIG. 4, exposing the components within the axial actuator.
Figure 6:
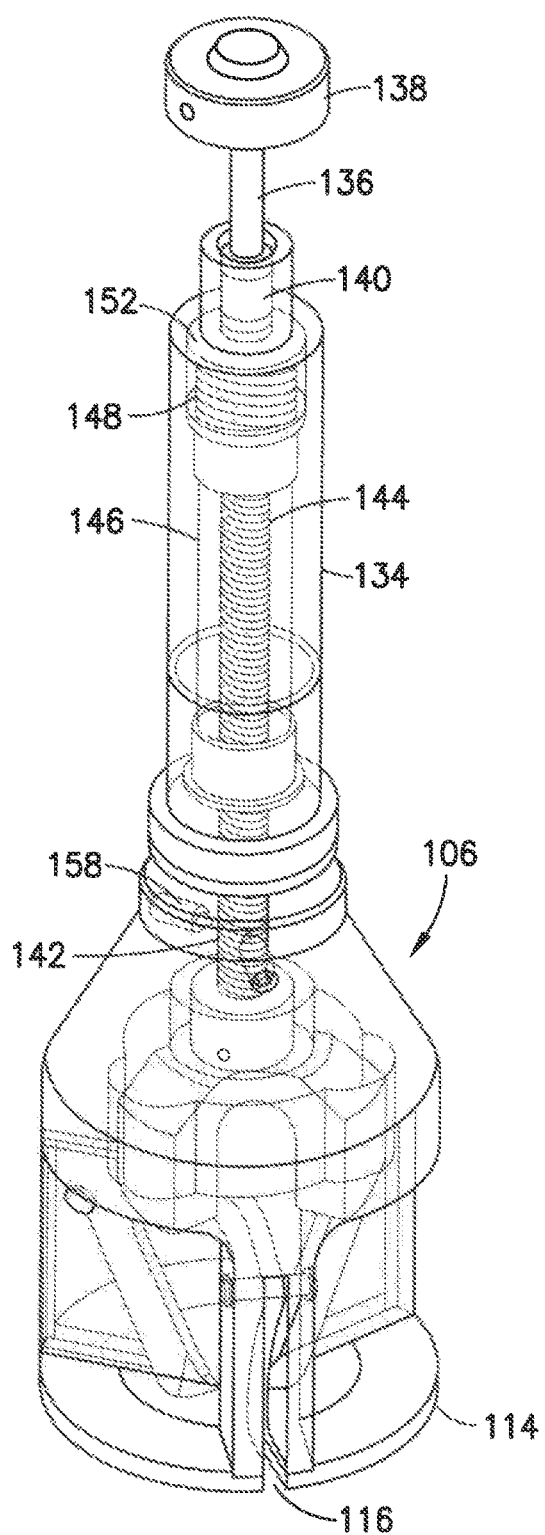
FIG. 6 is a perspective view of the universal capper/decapper shown in FIG. 4, exposing the components within the axial actuator and the capper/decapper housing;.
Figure 7:
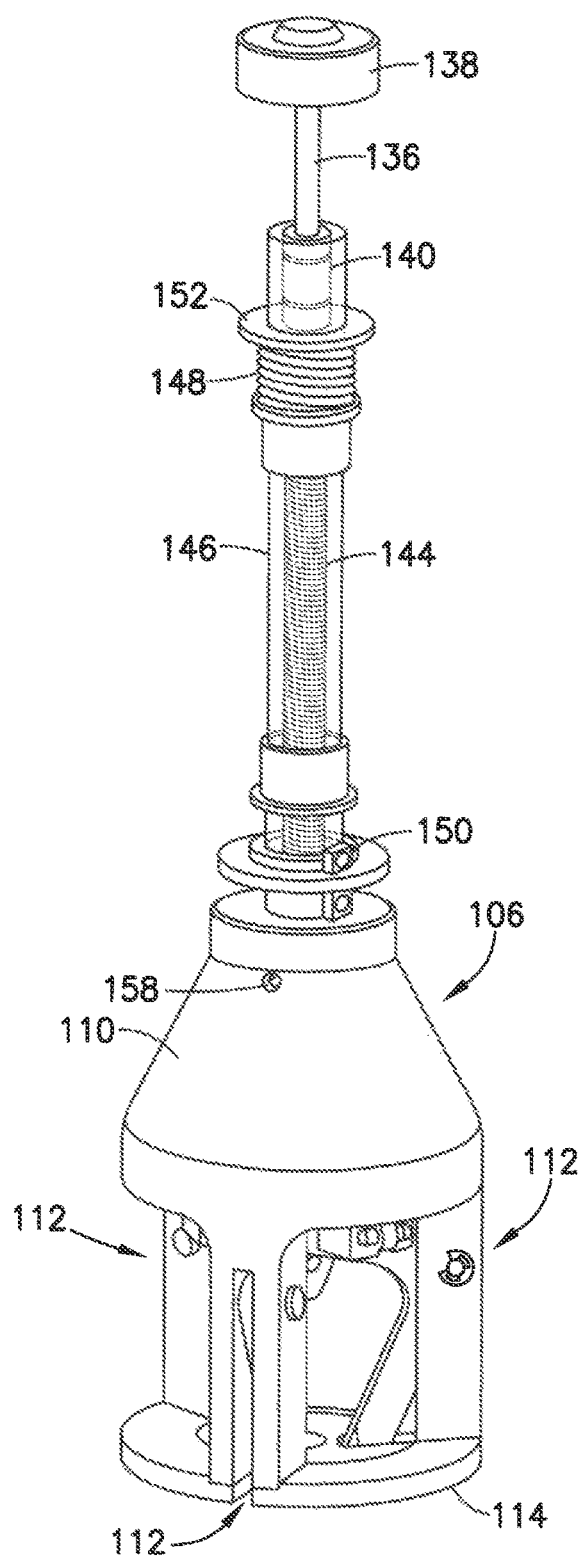
FIG. 7 is a perspective view of the universal capper/decapper shown in FIG. 5, with the cylindrical housing of the axial actuator removed.
Figure 8:
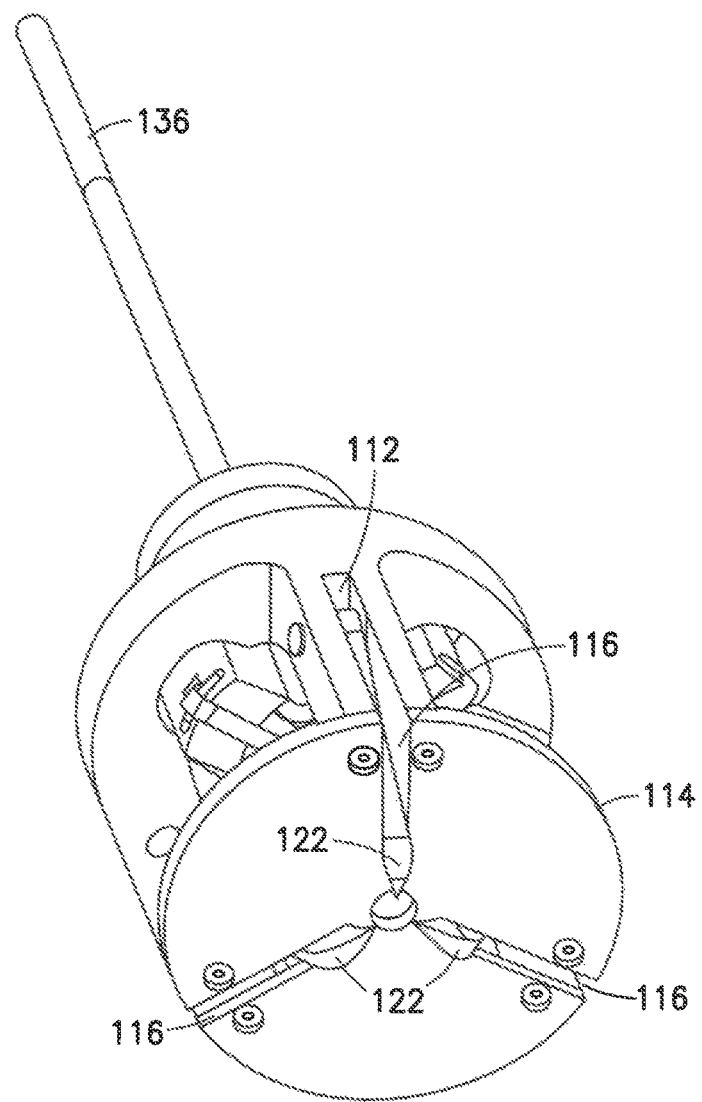
FIG. 8 is a bottom perspective view of the universal capper/decapper.

The capper/decapper housing 106 may also have a base plate 114 that is secured to the side wall 110 at the lower end thereof As shown in FIG. 8, the base plate 114 includes at least one radially-extending slot 116 that is aligned with the radially-extending channel 112.

Preferably, the universal capper/decapper 100 also includes a rotational actuator 118. As will be explained, the rotational actuator 118 is coupled to the capper/decapper housing 106 (via the axial actuator 104), and is configured to rotate the capper/decapper housing 106 about its axis of rotation. Although the capper/decapper assembly 102 is shown being substantially vertical (and having a vertical axis of rotation), the capper/decapper assembly 102 is not limited to this orientation. Nevertheless, for convenience, the universal capper/decapper 100 will be described assuming the vertical orientation.

As shown, preferably the capper/decapper assembly 102 has a plurality of the gripper arms 108, a plurality of the radially-extending channels 112, and a plurality of the radially-extending slots 116. Therefore, preferably each gripper arms 108 is pivotally received within a respective one of the radially-extending channels 112. Further, preferably the gripper arms 108, the channels 112 and the slots 116 are disposed substantially equidistantly around the circumference of the housing 106, and each slot 116 is aligned with a respective one of the channels 112. More preferably, the capper/decapper assembly 102 has three of the gripper arms 108, three of the radially-extending channels 112, and three of the radially-extending slots 116.

Figure 11:
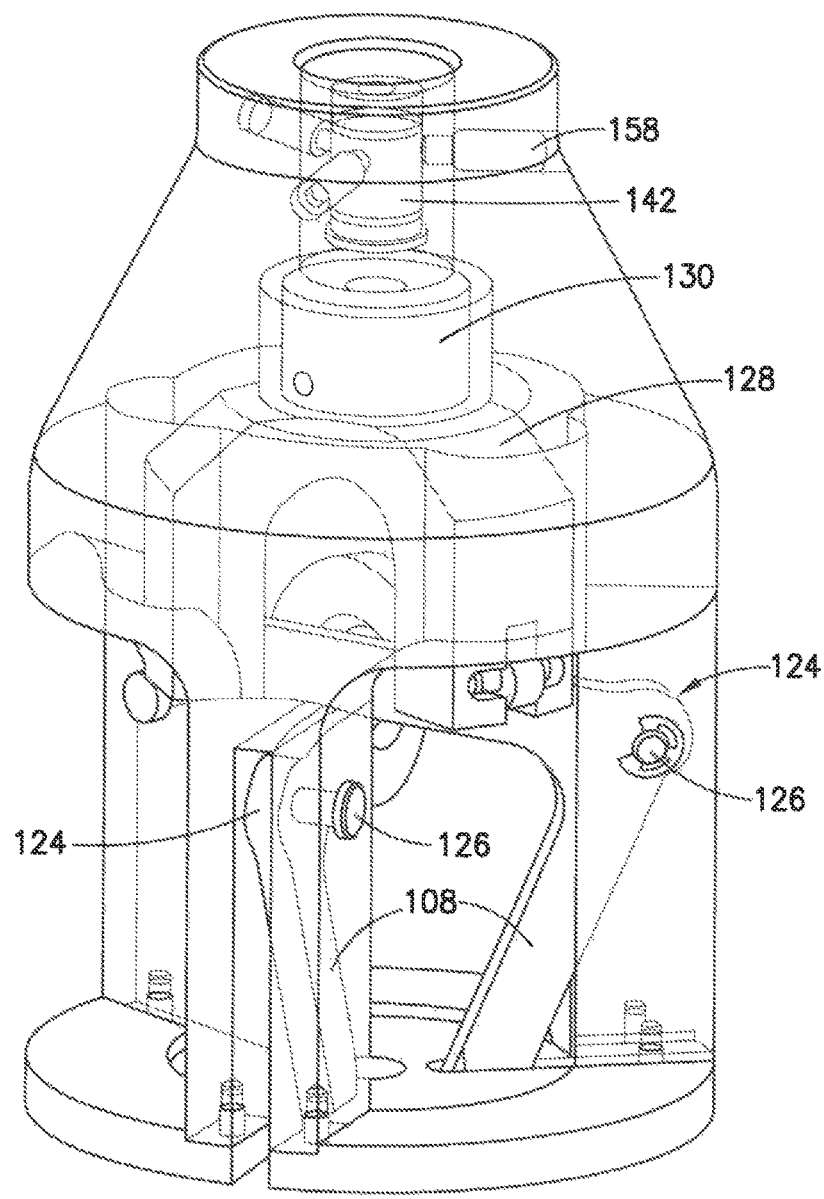
FIG. 11 is a perspective view of the universal capper/decapper shown in FIG. 9, exposing the yoke and gripper arms within the capper/decapper housing.
Figure 12:
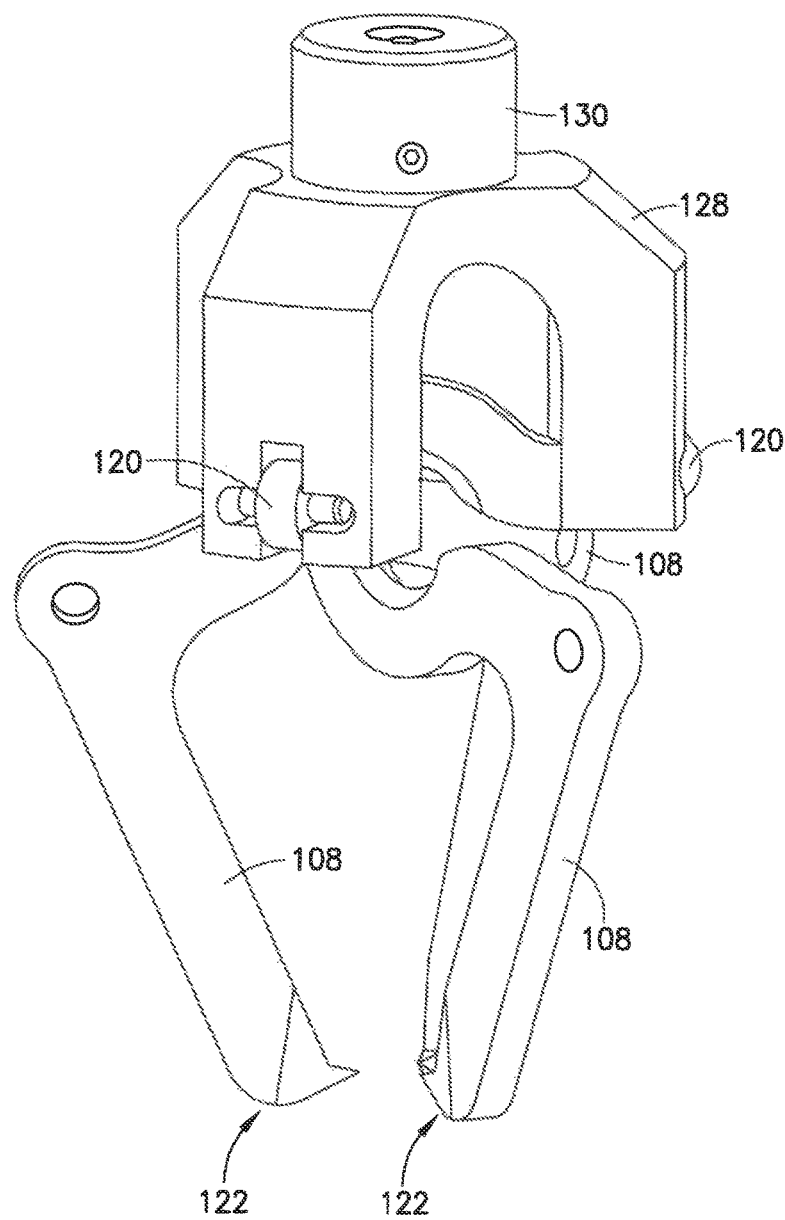
FIG. 12 is a magnified side perspective view of the yoke and the gripper arms.
Figure 13:
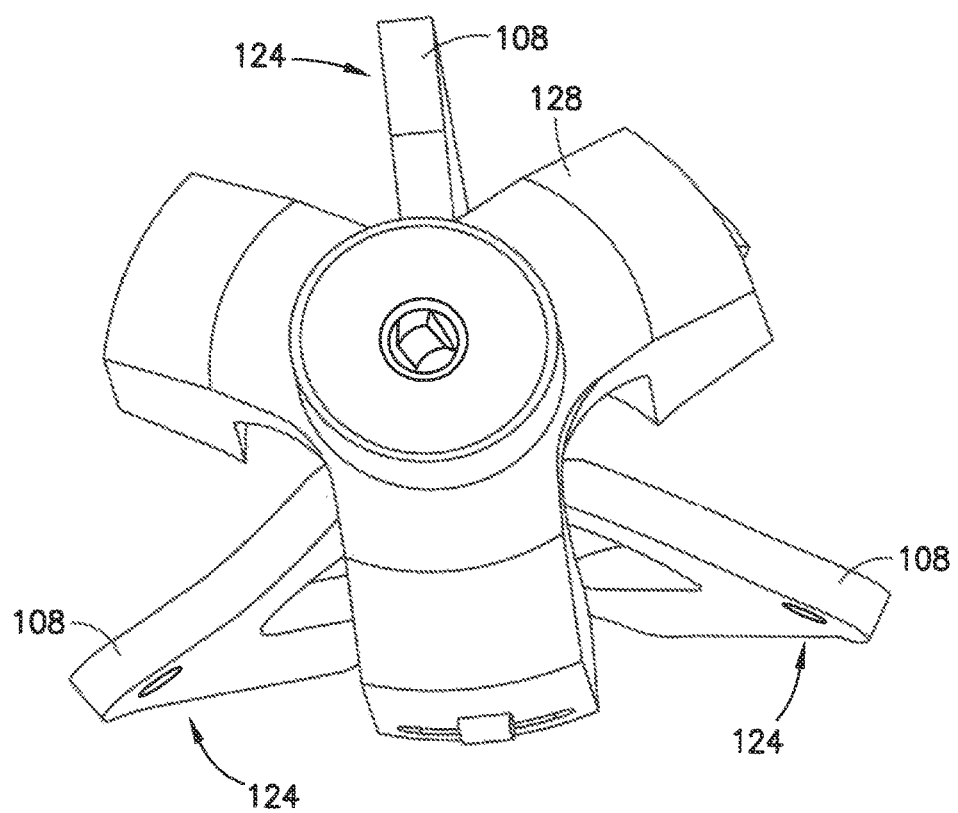
FIG. 13 is a top perspective view of the yoke and the gripper arms.
Figure 14:
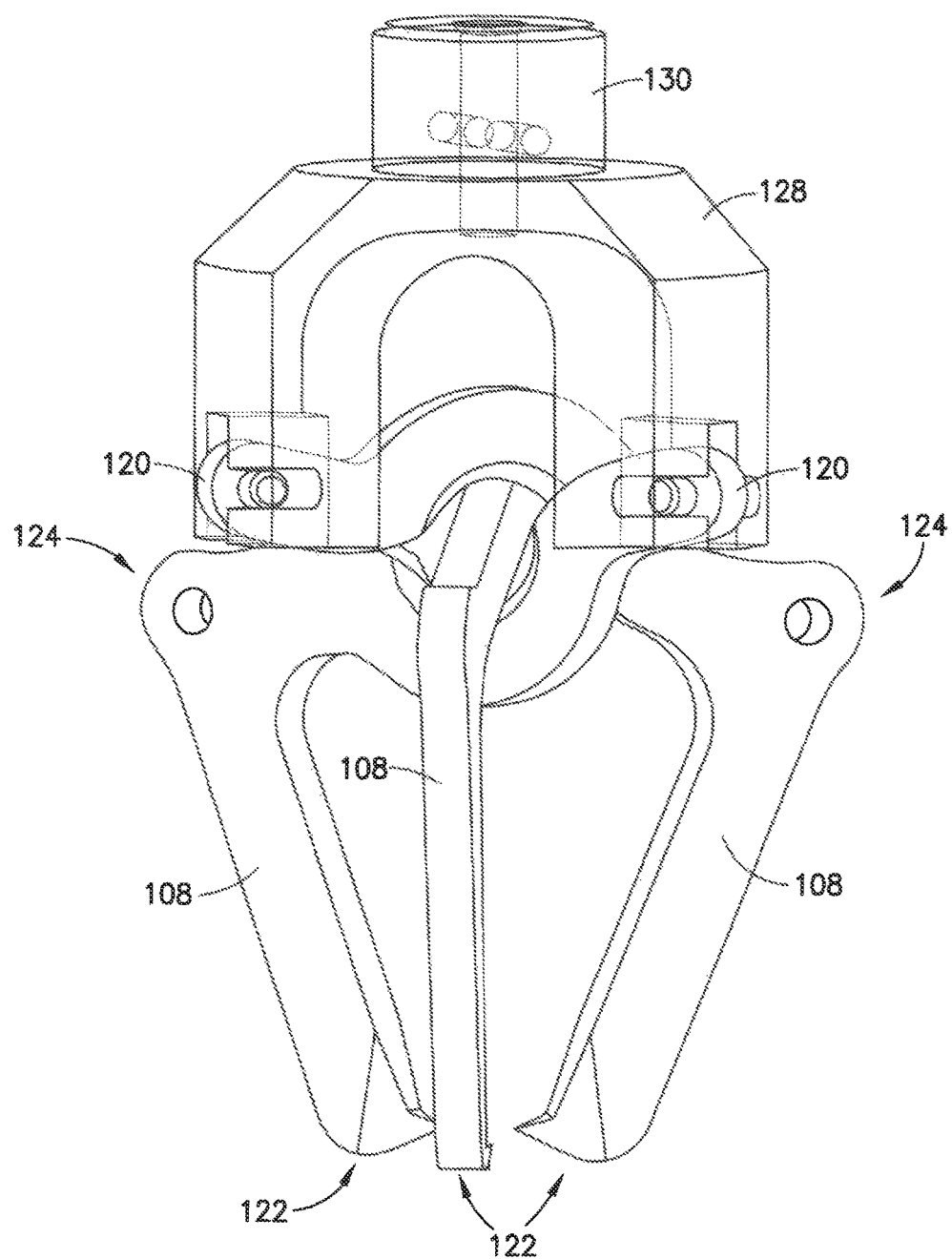
FIG. 14 is a magnified side perspective view of the gripper arms, with the yoke being transparently depicted.

As shown in FIGS. 11, 12 and 14, each gripper arm 108 may have a driven end 120, a gripper end 122, and a knee portion 124 that is disposed between the driven end 112 and the gripper end 122. The knee portion 124 of each gripper arm 108 is disposed within a respective channel 112 of the capper/decapper housing 106, and each slot 116 is configured to receive a respective gripper end 122 therein. As shown, each gripper arm 108 has a substantially L-shaped configuration, although other configurations of the gripper arm 108 are encompassed herein.

Each gripper arm 108 may be pivotally coupled to the capper/decapper housing 106 proximate the knee portion 124 via a mounting pin 126 that extends through the knee portion 124 and the respective side wall channel 112. As a result, each base plate slot 116 receives a respective gripper end 122 therein. The mounting pins 126 may be retained within the respective channel 112 via circlips that are provided on the opposite ends of the mounting pins 126.

The capper/decapper assembly 102 may also comprise a yoke 128 and a bearing 130, both disposed within the capper/decapper housing 106. The yoke bearing 130 is mounted to the yoke 128, at the upper end thereof, and can rotate about the axis of rotation of the capper/decapper housing 106. The driven ends 120 of the gripper arms 108 may be pivotally coupled to the yoke 128. Preferably, the driven ends 120 are pivotally coupled to the yoke 128, at the lower end thereof. Therefore, axial movement of the yoke 128 (in a direction parallel to the axis of rotation of the capper/decapper assembly 102) relative to the capper/decapper housing 106 causes the gripper arms 108 to rotate about their respective knee portions 124 relative to the capper/decapper housing 106, within their respective side wall channels 112 and base plate slots 116.

The axial actuator 104 is coupled to the capper/decapper assembly 102. As will be explained, the axial actuator 104 is coupled to the driven end 112 of each gripper arm 108, and is configured to drive the gripper ends 122 of the gripper arms 108 in a radial direction relative to the axis of rotation of the capper/decapper assembly 102 by rotating the gripper arms 108 about their respective knee portions 124 relative to the capper/decapper assembly 102. To effect this movement of the gripper arms 108, the axial actuator 104 may drive the yoke 128 (and hence the driven ends 112 of the gripper arms 108) in an axial direction that is substantially parallel to the axis of rotation of the capper/decapper assembly 102.

As shown in FIGS. 3 to 6, the axial actuator 104 may comprise a rod actuator (discussed below), a housing positioning damper (discussed below), and an annular driven gear 132. The rod actuator and the housing positioning damper may be provided within a common cylindrical member 134, and the annular driven gear 132 may be secured to the cylindrical member 134 at one end thereof.

The rod actuator drives the gripper ends 122 radially inwards and outwards, and may comprise an elongate shaft 136, and a linear actuator (not shown) coupled to the elongate shaft 136. The elongate shaft 136 may be coupled to the yoke 128. Preferably, the elongate shaft 136 is secured at the lower end thereof to the yoke bearing 130, and the rod actuator is configured to drive the driven ends by moving the yoke 128 in a direction substantially parallel to the axis of rotation of the capper/decapper assembly 102.

The rod actuator may also include an upper cylindrical bearing 138 that is secured to the elongate shaft 136 at the upper end thereof Preferably, the linear actuator is coupled to the elongate shaft 136 via the upper bearing 138, and is configured to drive the elongate shaft 136 in an axial direction that is substantially parallel to the axis of rotation of the capper/decapper assembly 102.

The rod actuator may also include a spring actuator mechanism that is coupled to the elongate shaft 136 and is configured to urge the gripper ends 122 radially inwards towards each other. The spring actuator mechanism may comprise a cylindrical collar 140, a lower cylindrical bearing 142, and an inner coil spring 144. The cylindrical collar 140 may be secured to the elongate shaft 136 at the upper end thereof. Preferably, the lower cylindrical bearing 142 is secured to the capper/decapper housing 106 via retaining screws 158, and the elongate shaft 136 is slidably received within the lower cylindrical bearing 142. The inner coil spring 144 may be disposed around the elongate shaft 136, and extends between the cylindrical collar 138 and the lower cylindrical bearing 142.

With this configuration, the inner coil spring 144 is coupled at one end to the elongate shaft 136 (via the cylindrical collar 140) and at the opposite end to the capper/decapper housing 106 (via the lower cylindrical bearing 142). As a result, the inner coil spring 144 resiliently urges the upper end of the elongate shaft 136 away from the capper/decapper assembly 102, which in turn resiliently urges the yoke 128 axially upwards and the gripper ends 122 radially inwards.

The housing positioning damper of the axial actuator 104 allows for limited axial movement in the vertical position of the capper/decapper assembly 102. The housing positioning damper may comprise an inner tubular member 146, and an outer coil spring 148. The tubular member 146 may be disposed within the cylindrical member 134. Preferably, the tubular member 146 is fitted with a key 150, at the lower end thereof, that is slidably received within respective recesses of the cylindrical member 134 and the capper/decapper housing 106. The outer coil spring 148 may be disposed within the cylindrical member 134, and extend between the upper end of the inner tubular member 146 (around the inner coil spring 144) and a stop ring 152 that is provided at the upper end of the cylindrical member 134. When the capper/decapper assembly 102 is suspended by the cylindrical member 134, and a container is moved axially upwards against the base plate 114, the resulting upwards force by the capper/decapper housing 106 against the key 150 will cause the tubular member 146 to move upwards against the outer coil spring 148, causing the outer coil spring 148 to compress. Therefore, with this configuration, the outer coil spring 148 allows for limited axial play in the vertical position of the capper/decapper housing 106.

The rotational actuator 118 may comprise a servo motor 154, and a pinion 156 that is driven by the servo motor 154 and drives the annular driven gear 132. Since the cylindrical member 134 and the capper/decapper assembly 102 are coupled together via the key 150, rotational movement of the annular driven gear 132 (via the pinion 156) is transferred to the capper/decapper assembly 102 via the key 150. As a result, the rotational actuator 118 is able to rotate the capper/decapper assembly 102 about its axis of rotation.

To remove the screw cap from a container using the universal capper/decapper 100, the linear actuator of the axial actuator 104 is activated, which causes the elongate shaft 136 of the rod actuator to move axially downwards. The resulting downwards force on the yoke 128 causes the driven ends 122 of the gripper arms 108 to move axially downwards, and the gripper arms 108 to pivot about their respective knee portions 124. As a result, the gripper ends 122 of the gripper arms 108 move radially outwards.

When the gripper ends 122 are fully separated, a container is moved vertically upwards (e.g. via an assembly line station) until the container screw cap engages the base plate 114 of the capper/decapper housing 106. Any further upwards movement of the container is accommodated by the housing positioning damper of the axial actuator 104.

The linear actuator is then deactivated, which causes the spring actuator mechanism of the rod actuator to move the elongate shaft 136 axially upwards. The resulting upwards force on the yoke 128 causes the driven ends 122 of the gripper arms 108 to move axially upwards, and the gripper arms 108 to pivot about their respective knee portions 124. As a result, the gripper ends 122 of the gripper arms 108 move radially inwards until the gripper ends 122 engages the sides of the container screw cap.

The rotational actuator 118 is then activated, which causes the capper/decapper assembly 102 to rotate about its axis of rotation in the direction required for removing the container screw cap from the container. During this step, the container is prevented from rotation (e.g. by the assembly line station). As a result, the rotational movement of the capper/decapper assembly 102 causes the screw cap to be removed from the container. The rotational actuator 118 is deactivated after the screw cap is fully disengaged from the container.

To replace/install the container screw cap, the container is moved vertically upwards (eg. via an assembly line station) until the container engages the bottom of the container screw cap that is held by the gripper ends 122 of the gripper arms 108. Any further upwards movement of the container is accommodated by the housing positioning damper of the axial actuator 104.

The rotational actuator 118 is then activated, which causes the capper/decapper assembly 102 to rotate about its axis of rotation in the direction required for attached the container screw cap to the container. During this step, the container is prevented from rotation (e.g. by the assembly line station). As a result, the rotational movement of the capper/decapper assembly 102 causes the screw cap to be secured to the container. The rotational actuator 118 is deactivated after the screw cap is fully engaged with the container.

The linear actuator of the axial actuator 104 is then activated, which causes the elongate shaft 136 of the rod actuator to move axially downwards. The resulting downwards force on the yoke 128 again causes the driven ends 122 of the gripper arms 108 to move axially downwards, and the gripper ends 122 of the gripper arms 108 move radially outwards.

After the gripper ends 122 are separated from the sides of the container cap, the container is moved vertically downwards (eg. via the assembly line station) until the container screw cap is disengaged from the base plate 114 of the capper/decapper housing 106.

The linear actuator is then deactivated, which causes the spring actuator mechanism of the rod actuator to move the elongate shaft 136 axially upwards. The resulting upwards force on the yoke 128 causes the driven ends 122 of the gripper arms 108 to move axially upwards, and the gripper ends 122 of the gripper arms 108 move radially inwards.

Since the gripper ends 122 can move radially inwards until the gripper arms 108 reach the inner radial limits of the base plate slots 116, and can move radially outwards until the gripper arms 108 reach the upper axial limits of the side wall channels 112, the universal capper/decapper 100 can accommodate screw caps of varying sizes. Further, since the radially inward movement of the gripper ends 122 is controlled by the spring actuator mechanism of the rod actuator, the universal capper/decapper 100 can accommodate such variation in cap sizes without recourse to complex control software.

The invention claimed is:

1. A universal container capper/decapper comprising:
a capper/decapper assembly comprising a capper/decapper housing having an axis of rotation, and at least one gripper arm, the at least one gripper arm having a driven end, a gripper end, and a knee portion intermediate the driven end and the gripper end, the at least one gripper arm being pivotally coupled to the capper/decapper housing proximate the knee portion at a first location;
the driven end extending radially inwardly from the knee portion toward the axis of rotation such that the driven end of the at least one gripper arm crosses the axis of rotation of the housing; and
an axial actuator coupled to the driven end of the gripper arm at a second location,
wherein, when the axial actuator is actuated, the second location translates in an axial direction with the axial actuator and the gripper end is driven in a radial direction relative to the axis of rotation of the capper/decapper housing by pivoting the gripper arm about the knee portion relative to the housing.

2. The container capper/decapper according to claim 1, wherein the axial actuator is configured to rotate the at least one gripper arm by driving the driven end in a direction substantially parallel to the axis of rotation.

3. The container capper/decapper according to claim 2, wherein the capper/decapper assembly further comprises a yoke disposed within the housing, and the driven end is pivotally coupled to the yoke.

4. The container capper/decapper according to claim 3, wherein the axial actuator comprises a rod actuator coupled to the yoke and configured to drive the driven end by moving the yoke in a direction substantially parallel to the axis of rotation.

5. The container capper/decapper according to claim 2, wherein the capper/decapper housing comprises a side wall, the side wall includes at least one radially-extending channel, and the at least one gripper arm is pivotally received within the at least one radially-extending channel.

6. The container capper/decapper according to claim 1, wherein the capper/decapper assembly further comprises a yoke disposed within the housing, and the driven end is pivotally coupled to the yoke.

7. The container capper/decapper according to claim 6, wherein the axial actuator comprises a rod actuator coupled to the yoke and configured to drive the driven end by moving the yoke in a direction substantially parallel to the axis of rotation.

8. The container capper/decapper according to claim 7, wherein the rod actuator comprises an elongate shaft, and a linear actuator coupled to the elongate shaft, the elongate shaft being coupled to the yoke.

9. The container capper/decapper according to claim 8, wherein the rod actuator further comprises a spring actuator mechanism coupled to the elongate shaft and configured to urge the gripper end radially inwards.

10. The container capper/decapper according to claim 9, wherein the spring actuator mechanism comprises a coil spring disposed around the elongate shaft and coupled at one end to the elongate shaft and at an opposite end to the capper/decapper housing.

11. The container capper/decapper according to claim 6, wherein the capper/decapper housing comprises a side wall, the side wall includes at least one radially-extending channel, and the at least one gripper arm is pivotally received within the at least one radially-extending channels.

12. The container capper/decapper according to claim 1, wherein the capper/decapper housing comprises a side wall, the side wall includes at least one radially-extending channel, and the at least one gripper arm is pivotally received within the at least one radially-extending channel.

13. The container capper/decapper according to claim 12, wherein the capper/decapper housing further comprises a base plate disposed at a lower end of the side wall, the base plate comprising at least one radially-extending slot, the at least one radially-extending slot being aligned with the at least one radially-extending channel and being configured to receive the gripper end therein.

14. The container capper/decapper according to claim 1, further comprising a rotational actuator coupled to the axial actuator for rotating the capper/decapper assembly about the axis of rotation.

15. The container capper/decapper according to claim 1, comprising a plurality of the at least one gripper arm disposed substantially equidistantly around the capper/decapper housing.

16. The container capper/decapper according to claim 1, wherein the at least one gripper arm has a substantially L-shape.

17. A universal container capper/decapper comprising:
a capper/decapper assembly comprising a housing having an axis of rotation and a plurality of gripper arms each having a driven end, a gripper end, and a knee portion disposed between the gripper end and driven end, the knee portions being pivotally coupled to the housing, and the driven ends extending radially inwardly from the knee portions toward the axis of rotation such that the driven ends of the gripper arms cross the axis of rotation of the housing wherein the driven ends are coupled to an axial actuator at opposite sides of the axis of rotation;
wherein the axial actuator so coupled is configured to drive the gripper ends in a radial direction relative to the axis of rotation by pivoting the gripper arms about the knee portions.

18. The universal container capper/decapper of claim 17, wherein:
the axial actuator comprises a yoke, a rod actuator and a housing damper,
the driven ends are pivotally coupled to the yoke,
the rod actuator is coupled to and extends from the yoke, and the housing damper includes a coil spring and tubular member each surrounding at least a portion of the rod actuator.

19. The universal container capper/decapper of claim 17, wherein the axial actuator comprises a yoke having a plurality of arms extending from a central body portion, the plurality of arms are spaced at intervals about the axis of rotation, and each of the driven ends are pivotally coupled to a corresponding arm of the yoke.

20. A universal container capper/decapper comprising:
   a housing having an axis of rotation and first and second gripper arms each having a driven end, a gripper end, and a knee portion intermediate the driven end and gripper end, each knee portion being pivotally coupled to the housing and each driven end extending from the knee portions in a transverse direction relative to the axis of rotation such that the driven end of the first gripper arm crosses the driven end of the second gripper arm such that the driven ends of the first and second gripper arms are coupled to an axial actuator at locations opposite the axis of rotation;
   wherein the axial actuator is so coupled such that actuation of the axial actuator pivots the first and second gripper arms about the knee portions.

21. The universal container capper/decapper of claim 20, wherein:
   the axial actuator includes a yoke,
   the knee portion of the first gripper arm is coupled to the housing at a first location, and
   the driven end of the first gripper arm is pivotally coupled to the yoke at a second location beyond the axis of rotation from the first location.

22. The universal container capper/decapper of claim 20, wherein the axial actuator comprises a yoke having first and second arms extending from a central body portion, the first and second arms are spaced at intervals about the axis of rotation, and the driven end of the first gripper arm is pivotally coupled to the first arm of the yoke and the driven end of the second gripper arm is pivotally coupled to the second arm of the yoke.

\* \* \* \* \*